United States Patent [19]

Aiken et al.

[11] 4,454,348

[45] Jun. 12, 1984

[54] MANUFACTURE OF DIPHENYLAMINE

[75] Inventors: John E. Aiken, Allegheny County; Marvin C. Fields, Allegheny County; Robert M. Stickel, Municipality of Murrysville, Westmoreland County, all of Pa.

[73] Assignee: United States Steel Corporation, Pittsburgh, Pa.

[21] Appl. No.: 434,096

[22] Filed: Oct. 13, 1982

[51] Int. Cl.$^3$ .................... C07C 85/18; C07C 85/20
[52] U.S. Cl. .................................................. 564/435
[58] Field of Search ......................................... 564/435

[56] References Cited

U.S. PATENT DOCUMENTS

| 2,968,676 | 1/1961 | Potter et al. | 564/435 |
| 3,079,439 | 2/1963 | Potter | 564/435 |
| 3,118,944 | 1/1964 | Addis | 564/435 |
| 3,944,613 | 3/1976 | Naramoto et al. | 564/435 |

FOREIGN PATENT DOCUMENTS

| 1187628 | 2/1965 | Fed. Rep. of Germany | 564/435 |
| 1219034 | 6/1966 | Fed. Rep. of Germany | 564/435 |
| 2249089 | 4/1973 | Fed. Rep. of Germany | 564/435 |
| 1439838 | 6/1976 | United Kingdom | 564/435 |

Primary Examiner—Paul F. Shaver
Attorney, Agent, or Firm—William L. Krayer

[57] ABSTRACT

Diphenylamine is made by the reaction in the vapor phase of two moles of aniline with the consequent evolution of ammonia; surprisingly high yields and selectivities are obtained by maintaining a significant concentration of ammonia in the catalyst zone, preferably by using the ammonia as a carrier for the aniline.

6 Claims, No Drawings

MANUFACTURE OF DIPHENYLAMINE

BACKGROUND OF THE INVENTION

Prior to the present invention, it has been known that aniline may be condensed in the presence of certain catalysts to make diphenylamine and ammonia. See, for example, U.S. Pat. No. 2,098,039. It has been generally thought, however, that the reaction must take place either in the liquid phase or at temperatures well over 400° C.

The liquid state is a required condition for several previously patented processes, such as the one recited in U.S. Pat. No. 2,645,662. Other prior art references employ somewhat specific catalysts, as U.S. Pat. Nos. 2,656,389; 4,100,195 and 2,120,968.

In the relatively simple reaction of aniline with itself in the presence of a catalyst to form diphenylamine, ammonia is evolved. The equilibrium concentrations of diphenylamine as a function of the starting molar ratio of ammonia to aniline, for the aniline condensation reaction, are as follows, based on Vriens & Hill, I&EC, November, 1952.

TABLE I

| $NH_3$/Aniline Molar Ratio | Equilibrium Wt. % DPA in Aniline |
|---|---|
| 0 | 84 |
| 0.5 | 62 |
| 1.0 | 48.5 |
| 2.0 | 33.5 |
| 3.0 | 25.5 |

From this data, yields of diphenylamine from the reaction would, not surprisingly, appear to be suppressed by the presence of ammonia in the reaction zone.

Many of the workers in the prior art have made provisions in one way or another to remove the ammonia from the reaction site as soon as it is formed, usually to avoid suppressing the reaction. See, for example, column 2, line 5 of U.S. Pat. No. 2,820,829 and column 6, line 13 of U.S. Pat. No. 2,514,430. In U.S. Pat. No. 3,071,619, a liquid phase reaction is maintained with the bleeding off of ammonia from the reaction system—see column 2, lines 31-35.

The reader perhaps may be most interested in U.S. Pat. Nos. 2,968,676; 3,118,944 and 3,944,613. In the first-mentioned of these, a process is proposed in which an alumina catalyst is impregnated with aluminum fluoride and the reaction takes place in the vapor phase. In the second, a variety of conditions and functions are explored for the control of the vapor phase reaction, emphasizing the use of relatively high feed rates. In the third patent, an amorphous synthetic silica-alumina catalyst is employed for a liquid-phase reaction.

None of the above references employs ammonia as a carrier gas for the aniline into the reaction zone and/or to the catalyst, as we propose. While U.S. Pat. No. 2,082,815 suggests that the diphenylamine product can be used as a heat-exchange medium, this suggestion also falls short of my invention, which postulates that, among other purposes, the ammonia produced, if recycled to serve as a carrier for the aniline reactant, can serve as a heat sink for the reaction. The temperature range of our invention is especially noteworthy in view of U.S. Pat. No. 2,938,055, which carefully conserves energy while maintaining a high reaction temperature.

None of the above references utilizes a catalyst of the type we use under the temperature and phase conditions we use, the combination of which has provided exceptional selectivity and conversion rates. Also, most of the prior art for vapor phase reaction teaches that frequent catalyst regeneration is necessary to maintain catalyst activity. Our elimination of this need is commercially very significant.

SUMMARY OF THE INVENTION

Our invention is a process for catalytically condensing aniline to form diphenylamine and ammonia wherein the aniline is fed to the reaction zone in a carrier of nitrogen, ammonia, or no carrier gas at all.

The results of a pilot plant parametric study are shown in Table II.

TABLE II

| Pilot Unit - Aniline Operation | | | | | | |
|---|---|---|---|---|---|---|
| Aniline | | | $NH_3$ | | Results | |
| Flow g/hr | T °F. | P psig | l/hr | mols mol aniline | % DPA in Eff | DPA Selectivity |
| 78 | 690 | 125 | nil | nil | 22.7 | 94.1 |
| 87 | 691 | 125 | nil | nil | 19.43 | |
| 65 | 690 | 143 | nil | nil | 20.1 | |
| 61 | 690 | 112 | nil | nil | 19.84 | |
| 65 | 689 | 275 | nil | nil | 19.36 | |
| 108 | 692 | 50 | nil | nil | 18.05 | |
| 64 | 690 | 50 | 9.6 | .57 | 10.01 | |
| 149 | 689 | 50 | 99.3 | 2.4 | 6.84 | |
| 84 | 688 | 50 | 85 | 3.3 | 6.78 | |
| 109 | 688 | 50 | 6.0 | 0.18 | 7.65 | |
| 115 | 699 | 50 | 32.1 | 0.91 | 8.5 | |
| 86 | 699 | 50 | 29.7 | 1.13 | 7.0 | 98.5 |
| 73 | 699 | 40 | 38.2 | 1.72 | 6.7 | 98.4 |
| 97.3 | 698 | 40 | 71 | 2.39 | 3.1 | |
| 77 | 697 | 25 | 18.9 | 0.8 | 7.1 | |
| 76 | 697 | 44 | 14.2 | 0.61 | 7.6 | |
| 83* 48 | 697 | 46 | 9.3 | 0.37 | 9.9 | |
| 73 | 693 | 45 | 0.7 | 0.03 | 23.5 | 98.1 |
| 79 | 696 | 46 | 6.9 | 0.29 | 15.9 | |

*During this period 83 g/hr of aniline was fed to the reactor but only 48 g/hr was recovered.

In the pilot unit runs, a pipe reactor was used having a diameter of about 1¼" and about four feet in length, containing one liter of catalyst. The relatively low selectivity in the first set of figures of Table II was probably influenced by phenol present in the reactor from a previous use. The catalyst was in the form of ¼" spheres.

Bench-scale results, showing also the use of nitrogen as a carrier, are shown in Table III. In the bench-scale unit, the reactor had an internal diameter of ⅞", 18" in length, containing about 100 ml of catalyst having a spherical shape and a diameter of about ⅛".

TABLE III

| Bench Scale Unit - Aniline Operation | | | | | | |
|---|---|---|---|---|---|---|
| Aniline | | | Diluent | | Results | |
| Flow ml/hr | T °F. | P psig | $NH_3/N_2$ | l/hr | mols mol aniline | % DPA in Eff | DPA Selectivity |
| 8 | 707 | 45 | $NH_3$ | cover | — | 5.5 | |
| 8 | 710 | 30 | " | " | — | 5.2 | 98.0 |
| 8 | 707 | 50 | " | " | — | 4.1 | |

TABLE III-continued

Bench Scale Unit - Aniline Operation

| Aniline Flow ml/hr | T °F. | P psig | Diluent NH$_3$/N$_2$ | 1/hr | mols mol aniline | Results % DPA in Eff | DPA Selectivity |
|---|---|---|---|---|---|---|---|
| 8 | 712 | 130 | " | " | — | 2.8 | |
| 8 | 712 | 50 | " | " | — | 8.0 | 98.6 |
| 8 | 710 | 45 | " | " | — | 8.3 | |
| 8 | 710 | 40 | " | 5.95 | 2.80 | 4.2 | |
| 8 | 709 | 40 | " | .28 | 0.13 | 12.0 | 98.9 |
| 8 | 709 | 32 | " | cover | — | 9.3 | |
| 8 | 709 | 200 | N$_2$ | .57 | 0.27 | 10.1 | |
| 8 | 709 | 200 | " | .57 | 0.27 | — | |
| 8 | 696 | 170 | " | 2.83 | 1.33 | 9.9 | 98.5 |
| 8 | 685 | 165 | " | 5.10 | 2.40 | 10.5 | |
| 8 | 691 | 165 | " | 2.55 | 1.20 | 9.3 | 98.9 |
| 8 | 691 | 160 | " | 14.16 | 6.67 | 9.1 | |
| 8 | 693 | 105 | " | 1.42 | 0.67 | — | |
| 4 | 693 | 165 | " | 9.35 | 8.81 | 12.5 | |
| 4 | 693 | 165 | " | 6.60 | 6.22 | 10.7 | |
| 4 | 689 | 165 | " | 14.35 | 13.52 | 13.8 | |
| 4 | 693 | 165 | " | 0 | — | 12.5 | |
| 4 | 694 | 165 | " | 4.58 | 4.32 | 12.2 | |
| 4 | 696 | 170 | " | 3.85 | 3.63 | 14.7 | |
| 4 | 694 | 175 | NH$_3$ | .38 | 0.36 | 11.3 | |
| 6 | 698 | 40 | " | .01 | 0.01 | 9.7 | |
| 6 | 696 | 50 | " | 0 | — | 9.6 | |
| 6 | 653 | 20 | " | 0 | — | 4.9 | |
| 6 | 653 | 35 | " | 0 | — | 5.1 | |
| 6 | 653 | 30 | " | 0 | — | 3.5 | |
| 6 | 651 | 40 | " | 0 | — | 3.9 | 98.9 |
| 6 | 651 | 50 | " | 0 | — | 3.7 | |
| 6 | 698 | 28 | " | .03 | .02 | 4.7 | |
| 6 | 698 | 20 | " | .01 | .01 | 8.8 | |
| 6 | 698 | 50 | " | .02 | .01 | 10.0 | 99.0 |
| 6 | 712 | 20 | " | 0 | — | 12.4 | |
| 6 | 712 | 50 | " | 0 | — | 12.6 | |
| 6 | 712 | 15 | " | 0 | — | 12.6 | 98.8 |
| 6 | 712 | 25 | NH$_3$ | 0 | — | 12.0 | |
| 6 | 700 | <10 | None | — | — | 10.0 | |
| 6 | 700 | <10 | None | — | — | 9.6 | |
| 6 | 700 | <10 | None | — | — | 9.4 | |
| 6 | 700 | <10 | None | — | — | 9.8 | |
| 6 | 700 | <10 | None | — | — | 9.3 | |
| 6 | 700 | <10 | None | — | — | 8.9 | 99.0 |
| 6 | 700 | <10 | None | — | — | 10.2 | |

These favorable results for the vapor phase condensation of aniline were accomplished at temperatures of about 690° F. (365° C.). This is somewhat unexpected since the literature suggests that substantially higher temperatures are required to effect substantial vapor phase condensation of aniline. For example, Hoelscher and Chamberlain (I&EC 42, 1558, 1950) state that appreciable vapor phase condensation of aniline does not begin until 400° C. and optimum conversion calls for 460° C. In contrast, our invention is successful at temperatures between about 340° C. and 380° C., preferably about 360°-370° C. In addition, the need for catalyst regeneration is eliminated with our process.

Pressures employed may be from about 15 to about 200 psig, with no advantage discerned to any higher pressures. Preferably, the pressure will be about 15-50 psig.

For the collection of the data shown herein, we employed a commercial catalyst known as Alcoa H-151, an activated alumina which has been washed to remove sodium. The catalyst should comprise a maximum of about 20% silica (0-20% silica), preferably 1-3%, a maximum of 0.2% sodium (0-0.2% sodium), preferably less than 0.1%, and the balance alumina. We have also employed similar commercially available catalysts, such as Norton SA 6173, which has 99.85% alumina, 0.1% silica, and 0.15% sodium. The catalyst should also be very low in heavy metals and alkaline earth metals. The Norton catalyst, for example, has 0.06% iron.

Both the pilot and bench-scale runs were continuous, the bench-scale results being collected over a period of about a month and the pilot unit for over five weeks. The various readings shown were monitored regularly throughout the respective periods. In neither case, surprisingly, was there any indication of tar buildup, catalyst fouling, or any reason to regenerate the catalyst.

An analysis of crude diphenylamine from the vapor phase condensation of aniline (sample A) and crude diphenylamine from the liquid phase condensation of phenol/aniline (samples B and C) are shown in Table IV. The much higher selectivity of the aniline based process is seen (the more so since samples B and C are somewhat untypically high in diphenylamine—typically diphenylamine contents are about 91-92%). Moreover, it is seen that sample A has essentially no methyl diphenylamines whereas sample B has about 0.6% methyl diphenylamines. Methyl diphenylamines are particularly objectionable when diphenylamine is used in the rubber industry and they are particularly difficult to distill from diphenylamine. Consequently, their absence will give a purer product and simpler and cheaper refining equipment.

TABLE IV

| | Area % (Aniline & Phenol Free) | | |
|---|---|---|---|
| | -A | -B | -C |
| Unidentified eluting prior to phenol | 0.37 | 0.05 | 0.08 |
| o-Cresol | <.01 | 0.10 | 0.16 |
| n-Methylaniline | 0.06 | 0.04 | 0.03 |
| Toluidine | <.01 | 0.05 | 0.05 |
| $C_2$—substituted anilines | 0.12 | 0.52 | 0.36 |
| $C_3$—substituted anilines | 0.14 | 0.53 | 0.39 |
| Quinoline | 0.10 | 0.09 | 0.08 |
| Indole | 0.13 | 0.06 | 0.04 |
| Quinadine | 0.04 | 0.05 | 0.04 |
| Unidentified | <.01 | 0.04 | 0.01 |
| 3-Methylindole | 0.03 | 0.07 | 0.04 |
| Phenylether | <.01 | 0.59 | 0.61 |
| Dimethylquinolines | <.01 | 0.04 | 0.03 |
| Unidentified (M..W. 168) | <.01 | 0.08 | 0.06 |
| Dibenzofuran | 0.05 | 0.12 | 0.11 |
| Unidentified (M.W. 172) | <.01 | 0.13 | 0.10 |
| Unidentified (minimum 2) | <.01 | 0.02 | 0.04 |
| n-Methyldiphenylamine | <.01 | 0.09 | 0.05 |
| Unidentified (minimum 3) | <.01 | 0.06 | 0.04 |
| Diphenylamine | 98.02 | 93.18 | 94.49 |
| Methyldiphenylamine (& M. W. 195) | <.01 | 0.31 | 0.25 |
| Methyldiphenylamines | 0.03 | 0.16 | 0.12 |
| $C_3$—substituted DPA | <.01 | 0.08 | 0.05 |
| Unidentified | 0.03 | 0.12 | 0.11 |
| $C_2$—substituted DPA | <.01 | 0.04 | 0.03 |
| Acridine | 0.29 | 0.61 | 0.48 |
| $C_2$—substituted DPA | 0.04 | 0.10 | 0.07 |
| Carbazole | 0.15 | 0.32 | 0.26 |
| Unidentified | 0.07 | 0.09 | 0.10 |
| $C_3$—substituted DPA | 0.18 | 0.26 | 0.19 |
| Unidentified (minimum 6) | <.01 | 0.20 | 0.16 |
| Methylacridine | 0.14 | 0.39 | 0.36 |
| Unidentified | <.01 | 0.53 | 0.40 |
| Probably phenyl DPA (M.W. 245) | <.01 | 0.40 | 0.30 |
| Unidentified | <.01 | 0.47 | 0.32 |

While we may perform the reaction without any carrier at all, we also may use an inert carrier such as nitrogen, or even a reaction product, e.g. ammonia. Ammonia may be of particular interest because it is readily available and, as may be seen above, does not adversely affect the selectivity of the reaction. We may employ it in amounts up to three moles or more per mole of aniline preferably in amounts from about 0.1 to 1.5 moles ammonia per mole of aniline.

We claim:

1. Method of making diphenylamine comprising reacting aniline in the vapor phase to make diphenylamine and ammonia in the presence of a low-sodium activated alumina catalyst which contains a maximum of 20% silica and no more than 0.2% sodium at temperatures between about 340° C. and 380° C. and pressures between about 15 to about 200 psig.

2. Method of claim 1 wherein the temperature is between about 360°-370° C.

3. Method of claim 1 wherein the pressure of the reaction is about 15-50 psig.

4. Method of claim 1 wherein the catalyst contains a maximum of 1 to 3% silica and less than 0.1% sodium.

5. Method of claim 1 wherein the aniline is fed to the catalyst together with a carrier gas.

6. Method of claim 1 wherein the aniline is fed to the catalyst together with a carrier gas of ammonia in a molar ratio of ammonia to aniline of about 0.1 to 1 to about 1.5 to 1.

* * * * *